US00PP31517P2

(12) United States Plant Patent
van Sambeek

(10) Patent No.: US PP31,517 P2
(45) Date of Patent: Mar. 3, 2020

(54) ***COREOPSIS* PLANT NAMED 'DOCORGRANMOONS'**

(50) Latin Name: *Coreopsis grandiflora*
Varietal Denomination: Docorgranmoons

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/350,470

(22) Filed: Nov. 19, 2018

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./263.1, 417
See application file for complete search history.

(56) References Cited

PUBLICATIONS

New perennial varieties digest: Supplement to Greenhourse management. 2017. file:///C:/Users/kredden/Desktop/New%20Perennial%20varieties%202017.pdf. (Year: 2017).*

* cited by examiner

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Coreopsis* plant named 'Docorgranmoons', characterized by its upright and mounded plant habit; moderately vigorous growth habit; freely branching habit; dark green-colored leaves; freely flowering habit with numerous inflorescences per plant; double-type inflorescences with yellow orange-colored ray florets; and good garden performance.

1 Drawing Sheet

Botanical designation: *Coreopsis grandiflora*.
Cultivar denomination: 'SWEET MARMALADE'.

BACKGROUND OF THE INVENTION

The present invention relates to a new and distinct cultivar of *Coreopsis* plant, botanically known as *Coreopsis grandiflora*, and hereinafter referred to by the name 'Docorgranmoons'.

The new *Coreopsis* plant is a product of a planned breeding program conducted by the Inventor in Aalsmeer, The Netherlands. The objective of the breeding program is to create uniform *Coreopsis* plants with numerous double-type inflorescences.

The new *Coreopsis* plant originated from a self-pollination made by the Inventor in Aalsmeer, The Netherlands in July, 2013 of a proprietary selection of *Coreopsis grandiflora* identified as code number CP-0010, not patented. The new *Coreopsis* plant was discovered and selected by the Inventor as a single flowering plant from within the progeny of the stated self-pollination in a controlled environment in Aalsmeer in July, 2014.

Asexual reproduction of the new *Coreopsis* plant by vegetative cuttings in a controlled environment in Aalsmeer, The Netherlands since February, 2015 has shown that the unique features of this new *Coreopsis* plant are stable and reproduced true to type in successive generations.

SUMMARY OF THE INVENTION

Plants of the new *Coreopsis* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Docorgranmoons'. These characteristics in combination distinguish 'Docorgranmoons' as a new and distinct cultivar of *Coreopsis* plant:

1. Upright and mounded plant habit.
2. Moderately vigorous growth habit.
3. Freely branching habit.
4. Dark green-colored leaves.
5. Freely flowering habit with numerous inflorescences per plant.
6. Double-type inflorescences with yellow orange-colored ray florets.
7. Good garden performance.

Plants of the new *Coreopsis* differ from plants of the parent selection in the following characteristics:

1. Plants of the new *Coreopsis* are more compact than plants of the parent selection.
2. Inflorescences of plants of the new *Coreopsis* have more ray florets than inflorescences of plants of the parent selection.

Plants of the new *Coreopsis* can be compared to *Coreopsis grandiflora* 'Decoreo16', disclosed in U.S. Plant Pat. No. 25,241. Plants of the new *Coreopsis* differ from plants of 'Decoreo16' in the following characteristics:

1. Plants of the new *Coreopsis* are taller than plants of 'Decoreo16'.
2. Plants of the new *Coreopsis* are more freely branching than plants of 'Decoreo16'.

3. Plants of the new *Coreopsis* have larger inflorescences than plants of 'Decoreo16'.
4. Inflorescences of plants of the new *Coreopsis* have larger, but fewer, ray florets than inflorescences of plants of 'Decoreo16'.

BRIEF DESCRIPTION OF THE PHOTOGRAPH

The accompanying photograph illustrates the overall appearance of the new *Coreopsis* plant. The photograph shows the colors as true as it is reasonably possible to obtain in colored reproductions of this type. Colors in the photographs may differ slightly from the color values cited in the detailed botanical description which accurately describe the colors of the new *Coreopsis* plant.

The photograph comprises a side perspective view of a typical flowering plant of 'Docorgranmoons' grown in a container.

DETAILED BOTANICAL DESCRIPTION

The aforementioned photograph and following observations and measurements describe plants grown in 13-cm containers in Aalsmeer, The Netherlands during the summer in an outdoor nursery and under conditions and cultural practices which approximate those generally used in commercial *Coreopsis* plant production. During the production of the plants, day temperatures averaged 22° C. and night temperatures averaged 17° C. Plants were pinched one time one week after planting and were four months old when the photograph and description were taken. In the following description, color references are made to The Royal Horticultural Society Colour Chart, 2007 Edition, except where general terms of ordinary dictionary significance are used. Measurements represent averages for typical flowering plants.

Botanical classification: *Coreopsis grandiflora* 'Docorgranmoons'.

Parentage:

*Female, or seed, parent*.—Proprietary selection of *Coreopsis grandiflora* identified as code number CP-0010.

*Male, or pollen, parent*.—Proprietary selection of *Coreopsis grandiflora* identified as code number CP-0010.

Propagation:

*Type*.—By vegetative cuttings.

*Time to initiate roots, summer*.—About twelve days at temperatures about 26° C.

*Time to initiate roots, winter*.—About two weeks at temperatures about 23° C.

*Time to produce a rooted young plant, summer*.—About two weeks at temperatures about 23° C.

*Time to produce a rooted young plant, winter*.—About 16 days at temperatures about 18° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright and mounding plant habit; broad inverted triangle; freely branching habit with about ten primary lateral branches each with about four secondary lateral branches; moderately vigorous growth habit and moderate growth rate.

*Plant height, soil level to top of foliar plane*.—About 19 cm.

*Plant height, soil level to top of floral plane*.—About 26 cm.

*Plant diameter or spread*.—About 30 cm.

*Lateral branches*.—Length: About 20 cm. Diameter: About 5 mm. Internode length: About 3 cm to 4 cm. Aspect: Upright to about 30° from vertical. Strength: Strong, flexible. Texture and luster: Pubescent; matte. Color: Close to 144B.

Leaf description:

*Arrangement*.—Opposite, simple; sessile.

*Length*.—About 10 cm.

*Width, with lobes*.—About 2.5 cm.

*Shape*.—Oblanceolate, entire to one or two-lobed.

*Apex*.—Acute.

*Base*.—Attenuate.

*Margin*.—Entire to deeply lobed; ciliate.

*Texture and luster, upper and lower surfaces*.—Pubescent; matte.

*Venation pattern*.—Pinnate.

*Color*.—Developing leaves, upper surface: Close to 137B. Developing leaves, lower surface: Close to 138B. Fully expanded leaves, upper surface: Close to 137A; venation, close to 137A. Fully expanded leaves, lower surface: Close to 138B; venation, close to 138B.

Inflorescence description:

*Appearance*.—Double-type terminal and axillary inflorescences with ray and disc florets arranged acropetally on a capitulum. Inflorescences positioned above and beyond the foliar plane on strong peduncles; inflorescences face mostly upright.

*Flowering habit*.—Freely flowering habit; about 45 inflorescences developing per plant.

*Fragrance*.—Faintly fragrant; pleasant.

*Time to flower*.—Under natural season conditions, plants flower from May to August in The Netherlands; plants begin flowering about seven weeks after planting.

*Post-production longevity*.—Inflorescences maintain good substance for about two weeks on the plant; inflorescences persistent.

*Inflorescence buds*.—Height: About 7 mm. Diameter: About 1 cm. Shape: Round, flat. Texture and luster: Smooth, glabrous; moderately glossy. Color: Close to 146A.

*Inflorescence size*.—Diameter: About 7 cm. Depth (height): About 2.6 cm. Disc diameter: About 1 cm. Receptacle height: About 5 mm. Receptacle diameter: About 1 cm. Receptacle color: Close to 144B.

*Ray florets*.—Quantity and arrangement: About 65 arranged in about five whorls. Length: About 3 cm. Width: About 1.5 cm. Shape: Obovate. Apex: Emarginate; ragged appearance. Base: Obtuse. Margin: Entire. Texture and luster, upper and lower surfaces: Smooth, glabrous; matte. Color: When opening, upper surface: Close to 14B. When opening, lower surface: Close to 12A. Fully developed, upper surface: Close to 14A; venation, close to 14A; with development, base of ray floret fading to closer to 17A. When opening, lower surface: Close to 12A; color does not change with development.

*Disc florets*.—Quantity and arrangement: About 55 arranged in about six whorls. Shape: Tubular, slender; apex dentate. Length: About 7 mm. Diameter: About 1 mm. Texture and luster: Smooth, glabrous; glossy Color, immature: Close to 15A. Color, mature: Close to 15A.

*Phyllaries*.—Quantity and arrangement: About eight in a single whorl. Length: About 1 cm. Width: About 7 mm. Shape: Deltoid. Apex: Acuminate. Base: Truncate. Margin: Entire. Texture and luster, upper and lower surfaces: Smooth, glabrous; slightly glossy. Color, upper and lower surfaces: Close to 152A.

*Peduncles*.—Length: About 17 cm. Diameter: About 2 mm. Strength: Strong. Aspect: Mostly upright. Texture and luster: Smooth, glabrous; moderately glossy. Color: Close to 138A.

*Reproductive organs*.—Androecium (present on disc florets only): Quantity per disc floret: Five. Filament length: About 2 mm. Filament color: Close to 2D. Anther shape: Rectangular. Anther length: About 3 mm. Anther color: Close to 166A. Pollen amount: Moderate. Pollen color: Close to 14A. Gynoecium (present on disc florets only): Quantity per floret: One. Pistil length: About 7 mm. Stigma diameter: About 3 mm. Stigma shape: Bi-parted. Stigma color: Close to 17A. Style length: About 7 mm. Style color: Close to 3D. Ovary color: Close to 155A.

*Seeds and fruits*.—To date, seed and fruit production has not been observed on plants of the new *Coreopsis*.

Pathogen & pest resistance: Plants of the new *Coreopsis* have not been shown to be resistant to pathogens and pests common to *Coreopsis* plants.

Garden performance: Plants of the new *Coreopsis* have exhibited good tolerance to rain and wind, have been observed to tolerate high temperatures about 35° C. and to be suitable for USDA Hardiness Zones 5 though 9.

It is claimed:

1. A new and distinct *Coreopsis* plant named 'Docorgranmoons' as illustrated and described.

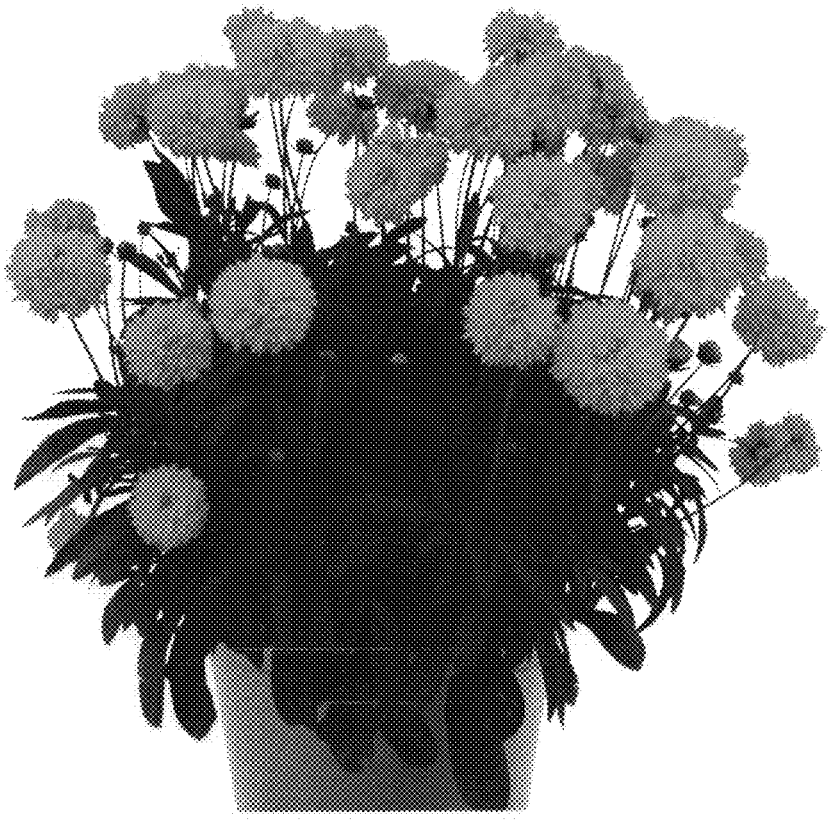

* * * * *